US00PP35068P3

(12) United States Plant Patent
Wright et al.

(10) Patent No.: US PP35,068 P3
(45) Date of Patent: Mar. 28, 2023

(54) BLUEBERRY PLANT NAMED 'C12-122'

(50) Latin Name: ***Vaccinium corymbosum* hybrid**
Varietal Denomination: C12-122

(71) Applicants: COSTA BERRY INTERNATIONAL PTY LTD, Ravenhall (AU); FLORIDA FOUNDATION SEED PRODUCERS, INC., Marianna, FL (US)

(72) Inventors: Gary Wright, Arrawarra Headland (AU); Paul M. Lyrene, Micanopy, FL (US)

(73) Assignees: COSTA BERRY INTERNATIONAL PTY LTD, Revenhall (AU); FLORIDA FOUNDATION SEED PRODUCERS, INC., Marianna, FL (US)

( * ) Notice: Subject to any disclaimer, the term of this patent is extended or adjusted under 35 U.S.C. 154(b) by 0 days.

(21) Appl. No.: 17/803,052

(22) Filed: Jan. 26, 2022

(65) Prior Publication Data

US 2022/0248586 P1 Aug. 4, 2022

Related U.S. Application Data

(60) Provisional application No. 63/206,160, filed on Jan. 29, 2021.

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ... A01H 5/08; A01H 5/00; A01H 5/02; A01H 6/36; A01H 6/368
See application file for complete search history.

(56) References Cited

U.S. PATENT DOCUMENTS

PP19,503 P3 * 11/2008 Lyrene ..... A01H 6/368 Plt./157
PP20,695 P2 * 2/2010 Wright ..... Plt./157

* cited by examiner

*Primary Examiner* — June Hwu
(74) *Attorney, Agent, or Firm* — Baker & McKenzie LLP

(57) ABSTRACT

The new blueberry plant variety 'C12-122' is provided. 'C12-122' is a commercial variety intended for the fresh market. The variety is produced from a cross of unpatented parents 'FL09-003' and 'FL08-013'.

5 Drawing Sheets

Latin name of the genus, and species:
Genus—*Vaccinium.*
Species—*corymbosum* hybrid.
Variety denomination: The new blueberry plant claimed is of the variety denominated 'C12-122'.

BACKGROUND OF THE INVENTION

The new variety 'C12-122' was selected from a population of seedlings derived from crossing the blueberry varieties known as 'FL09-003' (unpatented seed parent) and the variety known as 'FL08-013' (unpatented pollen parent). The cross was made in 2009 in Florida, USA and the seed was sown and grown on in Corindi Beach, New South Wales, Australia. The new variety was selected in 2012 from among plants located on land at Corindi Beach and assigned the breeding code 'C12-122'. Plants of 'C12-122' were propagated by cuttings for further evaluation and resulted to be uniform and stable. The new variety showed distinctive traits such as evergreen, vigorous, good size and firm fruit.

SUMMARY OF THE INVENTION

Asexual reproduction of the new variety 'C12-122' by cutting propagation since 2012 at Corindi Beach, New South Wales, Australia has demonstrated that the new variety reproduces true to type plants.

The new variety was selected in 2012 as a single plant within a population of seedlings resulting from controlled cross of *Vaccinium* varieties. The seedling population was planted in an experimental block in the field at Corindi Beach, New South Wales, Australia and the selection of the new variety took place in the same block. Selection criteria were a combination of early season crop, low chilling requirement, strong vigour, non-deciduous type of plant (evergreen) and very large fruit size. The new variety was subsequently evaluated for eight years at the commercial farm at Corindi Beach, New South Wales, Australia.

The following characteristics of the new variety have been repeatedly observed and can be used to distinguish 'C12-122' as a new and distinct variety of *Vaccinium corymbosum* hybrid:

1. Non-deciduous (Evergreen)
2. Early season crop
3. Upright growth habit
4. Low chilling requirement (estimated between 0 and 300 hours)
5. Very large fruit size, average 4.1 g
6. Firm fruit The new blueberry variety 'C12-122' has maintained its distinguished characteristics throughout successive asexual propagation. The variety has been repeatedly asexually reproduced through softwood cuttings in New South Wales, Australia and the clones are phenotypically identical to the original plant.

BRIEF DESCRIPTION OF THE DRAWINGS

The accompanying photographic illustration shows typical specimens in full color of the foliage and fruit of the new variety 'C12-122'. The colors are as nearly true as is reasonably possible in a color representation of this type.

Figure 1:
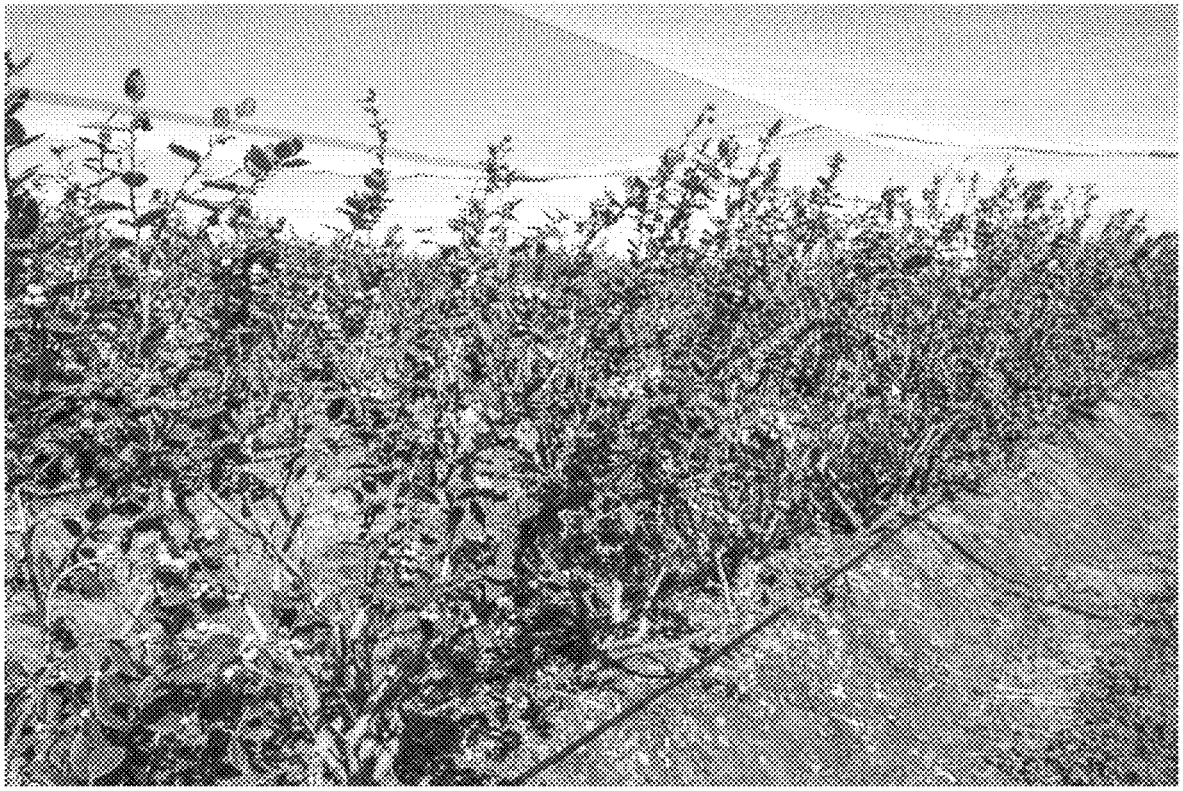
FIG. 1 is a photograph of the new variety 'C12-122', growing in soil. Photos show 6 year old plants.
Figure 2:
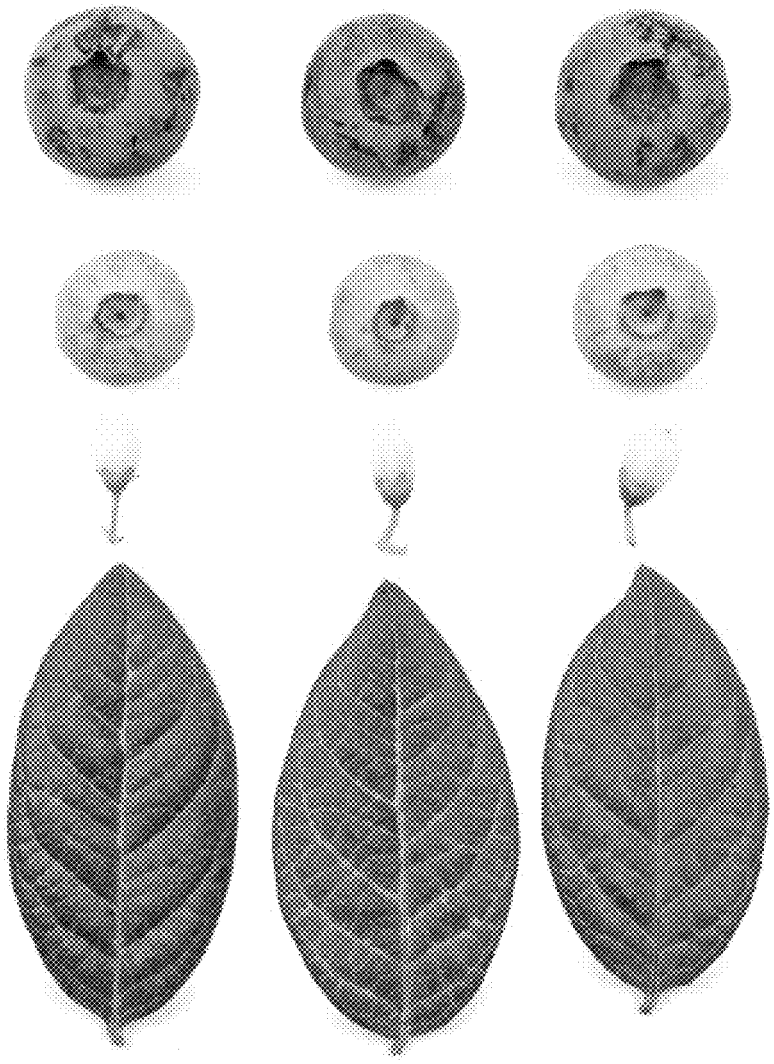
FIG. 2 is a photograph of the new variety 'C12-122', showing the botanical parts of the plants (blue fruit, green fruit, flowers and leaves).
Figure 3:
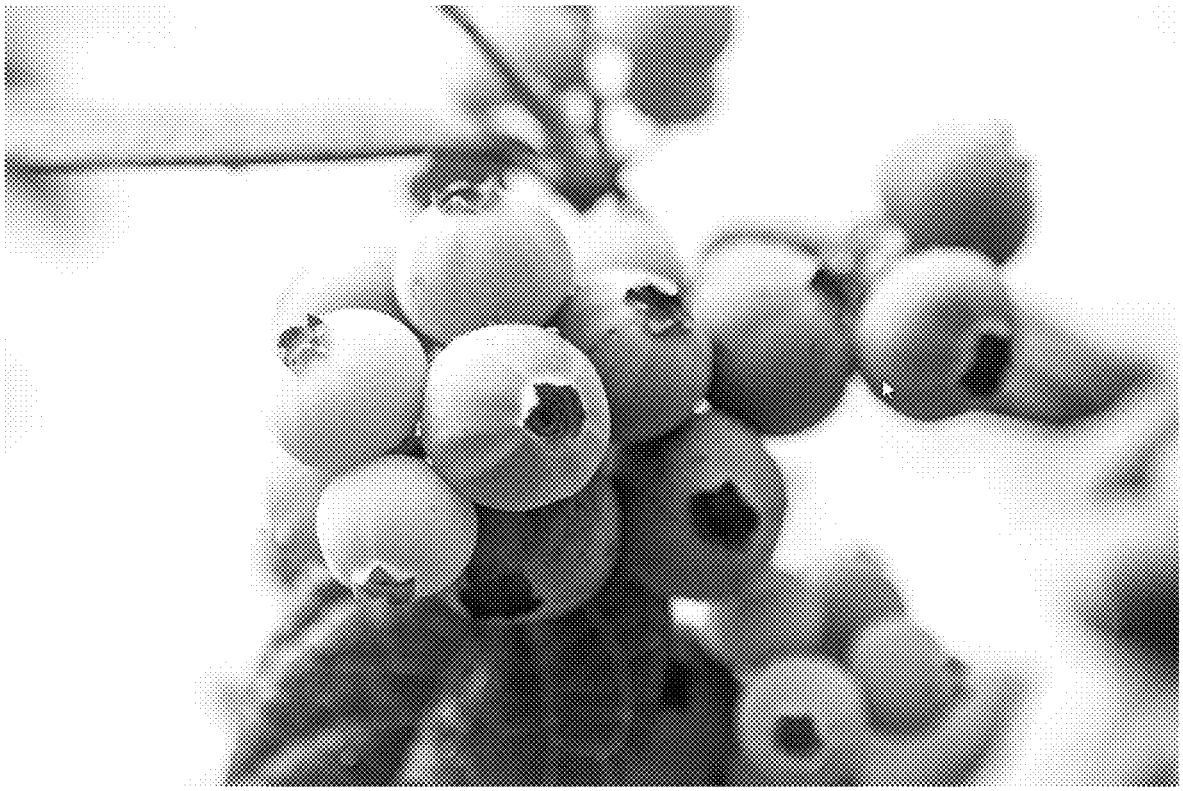
FIG. 3 is a photograph of the typical fruit cluster of the variety 'C12-122'.
Figure 4:
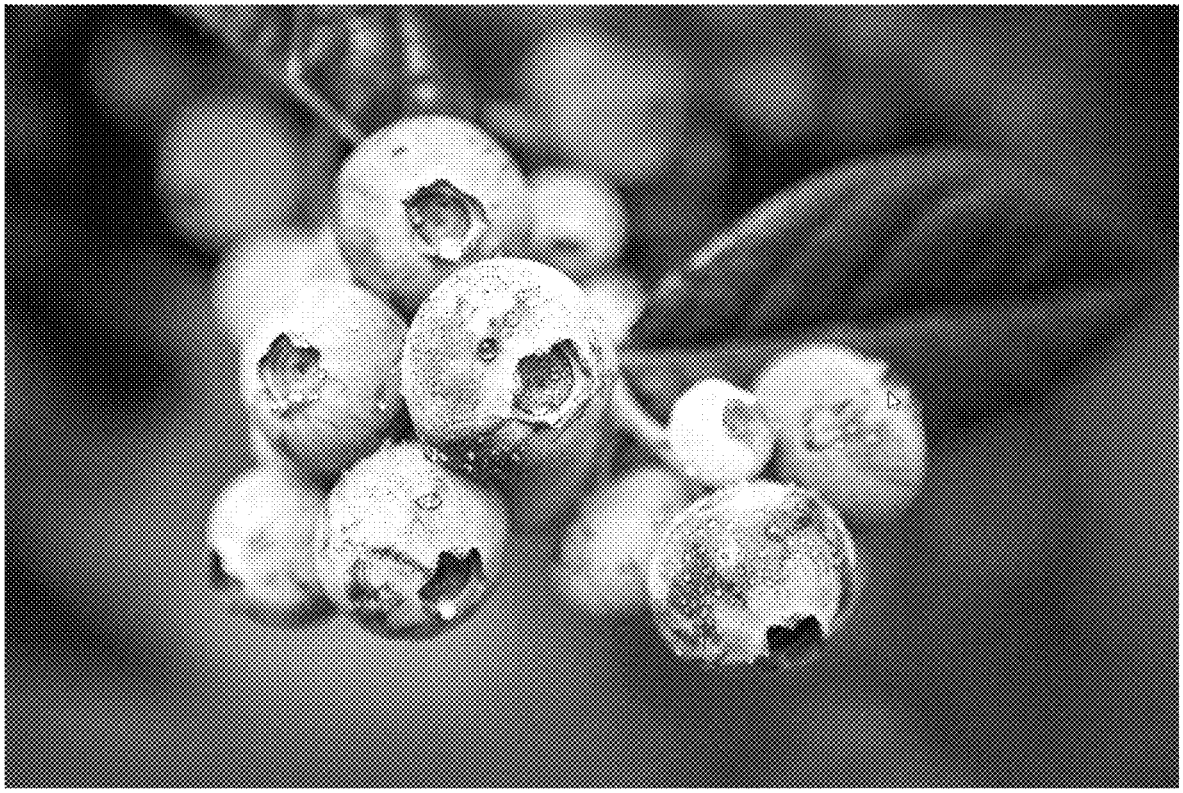
FIG. 4 is a photograph showing the large fruit size of the new variety 'C12-122'.
Figure 5:
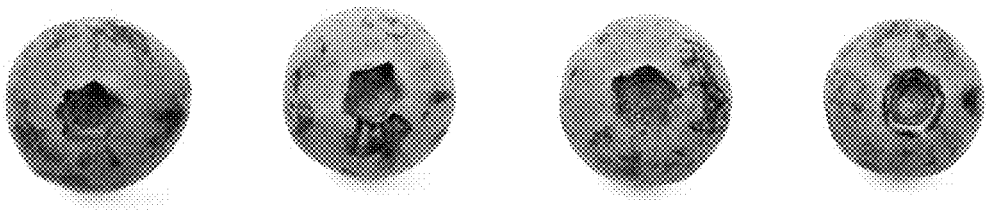
FIG. 5 is a photograph showing the typical fruit calyx of the variety 'C12-122'.

The colors in the photographs are as close as possible with the photographic and printing technology utilized. The color values cited in the detailed botanical description accurately describe the colors of the new blueberry.

DETAILED BOTANICAL DESCRIPTION

The following detailed description sets forth the distinctive characteristics of 'C12-122'. The data which defines these characteristics was collected from asexual reproductions of the original selection. Dimensions, sizes, colors, and other characteristics are approximations and averages set forth as accurately as possible. For all traits data was collected from 3 plant parts across 6 randomly selected plants. For the traits relating to fruits (e.g., fruit weight, firmness, brix, acidity) the data is an average across twenty fruits collected randomly. The plant history was taken on plants approximately 3 years of age, and the descriptions relate to plants grown in the field in Corindi Beach, New South Wales, 2456 Australia. Descriptions of fruit characteristics were made on fruit grown in Corindi Beach, New South Wales, 2456 Australia. Color designations are from the 2007 edition of The Royal Horticultural Society ("R.H.S.") Colour Chart. 'C12-122' has not been observed under all possible environments. The phenotype may vary slightly with different growing environments such as temperature, light, fertility, soil pH, moisture and maturity levels, but without any change in the genotype.

Classification:

*a. Family.*—Ericaceae.
*b. Genus.*—*Vaccinium.*
*c. Species.*—*corymbosum* hybrid.
*d. Common name.*—Blueberry.

Parentage: Female Parent—unpatented selection 'FL09-003'. Male Parent—unpatented selection 'FL08-013'.

Market class: Fresh market.

PLANT

General:

*Parentage.*—FL09-003 x FL08-013.
*Plant height.*—1.4 m.
*Plant width.*—1.1 m.
*Growth habit.*—Upright.
*Growth.*—Strong vigour.
*Productivity.*—High. Average of 6.5 Kg per plant (estimated equivalent production of 14.3 pounds per plant) from 3-year-old plants when growing in 17 L pots at Corindi Beach, NSW. The plants are spaced at 0.7 m apart along the row and 2.5 m between the rows, which gives an estimated plant density of 5700 plants per hectare.
*Cold hardiness.*—Low chill (USDA plant hardiness Zone 4).
*Cold tolerance.*—Low.
*Chilling requirement.*—Very low, estimated between 0 and 300 hours.
*Tolerance to disease.*—None assessed.
*Leafing.*—Overall medium, plant retains leaves during the winter in low chill environments (zone 4).
*Disease resistance.*—The variety is tolerant to blueberry leaf rust (*Thekopsora minima*).
*Heat tolerance.*—Moderately resistant to heat.
*Twigginess.*—Low.

STEM

General:

*Bark texture.*—Rough.
*One-year-old shoot's color designation.*—The base color is green group, similar to 139C.
*Mature cane length.*—0.73 m.
*Mature cane width.*—12.9 mm.
*Mature cane color.*—Grey-orange group, similar to 165A, with streak of grey-brown group, similar to 199B.
*Fall color on new shoots.*—Base color is green group, similar to 137C and with over color, red-purple group, similar to 59A.
*Surface texture of new wood.*—Smooth.
*Internode length on strong, new shoots.*—33.3 mm.
*Fruiting wood in length.*—40.0 cm.

FOLIAGE

General:

*Leaf color (top side).*—Green group, similar to N137B.
*Leaf color (under side).*—Yellow-green, similar to 147C.
*Leaf arrangement.*—Alternate.
*Leaf shape.*—Elliptic.
*Leaf margins.*—Entire.
*Leaf venation.*—Reticulate.
*Leaf length.*—Long to very long (69.9 mm).
*Leaf width.*—Broad (36.6 mm).
*Leaf length/width ratio.*—1.9.
*Shape of the leaf apex.*—Acute.
*Shape of the leaf base.*—Cuneate.
*Leaf nectaries.*—Absent.
*Pubescence of upper side.*—Absent.
*Pubescence of lower side.*—Absent.
*Attitude.*—Horizontal.

Petioles:

*Length.*—Average 3.7 mm.
*Width.*—Average 2 mm.
*Color.*—Yellow-green group 145A.
*Texture.*—Smooth.

FLOWERS

General:

*Time of beginning of flower.*—Early to mid-season (50% of anthesis estimated to be on the 15$^{th}$ of June, on 3 year old plants, cultivated at Corindi Beach, NSW).
*Flower shape.*—Urceolate.
*Flower fragrance.*—No.

Corolla:
- *Shape*.—Urceolate.
- *Color*.—White group NN155C.
- *Length*.—7.3 mm.
- *Width of widest region*.—7.3 mm.
- *Petal texture*.—Smooth.
- *Petal width (ridge to ridge)*.—4.54 mm.
- *Aperture diameter*.—Narrow, on average 3.04 mm.
- *Anthocyanin coloration of corolla*.—Absent or very weak.
- *Corolla ridges*.—Present, average of 5.
- *Protrusion of stigma*.—Present, but very small.

Calyx (with sepals):
- *Diameter*.—3.85 mm.
- *Color of sepal's outside*.—Green group, similar to 144B.
- *Color of sepal's inside*.—Green group, similar to 144D.

Inflorescence:
- *Inflorescence length (excluding peduncle)*.—Long, 27.5 mm.
- *Inflorescence width*.—24.58 mm.
- *Flower length (excluding pedicel)*.—10.4 mm.
- *Flower diameter*.—6.58 mm.
- *Flower length/width ratio*.—1.58.
- *Surface texture of peduncle*.—Medium (between rough and smooth).
- *Color of peduncle*.—Yellow-green group, similar to 145A, with greyed-red group, similar to 182A on top.
- *Length of flower pedicel*.—11.04 mm.
- *Surface texture of pedicel*.—Medium (between rough and smooth).
- *Color of pedicel*.—Group, similar to 146A and 146C.
- *Number of flowers per cluster*.—10 on average.
- *Flower cluster density*.—Dense.
- *Flowering interval on current year shoot*.—June to end of July.
- *Flowering interval on one-year old shoot*.—June to August.

Stamen:
- *Length*.—6.3 mm.
- *Number per flower*.—10.
- *Filament color*.—Yellow-green group 145C.

Pistil:
- *Pistil length (including ovary)*.—10.32 mm.
- *Style length (including stigma)*.—8.15 mm.
- *Style color*.—Yellow-green group, similar to N144B and 145B.

Anther:
- *Length*.—3.5 mm.
- *Number*.—10.
- *Color*.—Greyed-orange group, similar to 165A.

Pollen:
- *Abundance*.—Medium.
- *Color*.—Yellow group 11C.
- *Self-compatibility*.—Yes, this variety shows a high degree of self-compatibility and high degree of parthenocarpic fruit.

FRUIT

General:
- *Time of fruit ripening*.—Early, estimated 50% of the fruit ripe on the 15$^{th}$ of August, on 3 year old plants, growing at Corindi Beach, NSW.
- *Plant fruiting types*.—One-year-old and current seasons shoots.
- *Cluster density*.—Dense, 9 berries per cluster.
- *Unripe fruit color*.—Yellow-green-145A.
- *Ripe berry color*.—Blue group 103A, when bloom is removed.
- *Berry surface wax abundance*.—Strong.
- *Berry weight*.—Very large, average 4.1 g.
- *Berry height from calyx to scar*.—15.6 mm.
- *Berry diameter*.—20.1 mm.
- *Berry shape*.—Oblate.
- *Fruit diameter of calyx basin*.—Medium, on average 6.6 mm.
- *Fruit depth of calyx basin*.—Medium.
- *Fruit stem scar*.—Medium and dry.
- *Sweetness when ripe*.—Medium (12 Brix).
- *Firmness when ripe*.—Firm 191 g/mm, measured with FirmTech.
- *Acidity when ripe*.—Very high (1%).
- *Berry flesh color*.—Yellow-green group, similar to 145C and 145D.
- *Storage quality*.—Medium to long shelf life (average 24 days).
- *Suitability for mechanical harvesting*.—Not tested.
- *Self-fruitfulness*.—High, with a large proportion of the crop as parthenocarpic.
- *Uses*.—Fruit to be hand harvested for fresh market.

SEED

General:
- *Seed abundance in fruit*.—Very low, 1 seed per fruit.
- *Seed color*.—Greyed orange 165A.
- *Seed length*.—1.7 mm.

COMPARISON WITH SIMILAR CULTIVARS

Table 1 below provides a comparison between 'C12-122' and several similar cultivars:

TABLE 1

Comparison of 'C12-122' with similar cultivars.

| Characteristics | 'C12-122' | 'C99-42' (U.S. Plant Pat. No. 20,695P2) | 'Snowchaser' (U.S. Plant Pat. No. 19,503P3) |
|---|---|---|---|
| Plant vigour | Strong | Weak to medium | Medium |
| Plant growth habit | Upright | Semi-upright to intermediate | Semi-upright |
| One year old shoot length of internodes | Medium | Very short to short | Short |
| Leaf length | Long to very long | short | Long |
| Leaf length (mm) | 69.9 ± 4.7 | 53.10 ± 0.8 | 61.50 ± 0.9 |
| Leaf width | Broad | Very narrow to narrow | Broad |
| Leaf width (mm) | 36.6 ± 2 | 22.9 ± 1.3 | 34.3 ± 1.5 |
| Flower size of corolla | Small | Medium | Medium |
| Flower corolla length (mm) | 7.3 ± 0.4 | 9.7 ± 0.3 | 9.5 ± 0.3 |
| Fruit cluster density | Dense | Sparse | Medium |
| Fruit size | Very large | Small to medium | Small to medium |
| Fruit weight (g) | 4.1 ± 0.9 | 1.9 ± 0.39 | 1.7 ± 0.21 |
| Fruit diameter (mm) | 20.1 ± 1.7 | 15.6 ± 0.96 | 15.10 ± 0.97 |
| Fruit depth of calyx basin | Medium | Medium | Shallow |
| Fruit intensity of bloom | Strong | Weak to medium | Weak to medium |

TABLE 1-continued

Comparison of 'C12-122' with similar cultivars.

| Characteristics | 'C12-122' | 'C99-42' (U.S. Plant Pat. No. 20,695P2) | 'Snowchaser' (U.S. Plant Pat. No. 19,503P3) |
|---|---|---|---|
| Fruit firmness | Firm | Firm | soft |
| Soluble solid content (%) | 12 | 13.1 | 14 |
| Titratable acidity (%) | 1 | 0.4 | 0.7 |
| Time of vegetative bud burst | Late | Early | early |
| Time of beginning of flowering | Early | Early to medium | Very early to early |

TABLE 1-continued

Comparison of 'C12-122' with similar cultivars.

| Characteristics | 'C12-122' | 'C99-42' (U.S. Plant Pat. No. 20,695P2) | 'Snowchaser' (U.S. Plant Pat. No. 19,503P3) |
|---|---|---|---|
| Time of beginning of fruit ripening | Early | Early to medium | Very early to early |

The invention claimed is:

1. A new and distinct variety of blueberry plant named 'C12-122', substantially as illustrated and described herein.

* * * * *